United States Patent
Markosyan

(10) Patent No.: US 10,480,019 B2
(45) Date of Patent: *Nov. 19, 2019

(54) PROCESS FOR PRODUCING HIGH-PURITY RUBUSOSIDE

(71) Applicant: PureCircle Sdn Bhd, Kuala Lumpur (MY)

(72) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 313 days.

This patent is subject to a terminal disclaimer.

(21) Appl. No.: 14/560,403

(22) Filed: Dec. 4, 2014

(65) Prior Publication Data

US 2015/0118379 A1   Apr. 30, 2015

Related U.S. Application Data

(63) Continuation-in-part of application No. 14/380,071, filed as application No. PCT/MY2013/000051 on Mar. 7, 2013, application No. 14/560,403, which is a continuation-in-part of application No. 13/553,820, filed on Jul. 20, 2012, now Pat. No. 8,993,028.

(60) Provisional application No. 61/608,110, filed on Mar. 8, 2012, provisional application No. 61/522,237, filed on Aug. 10, 2011.

(51) Int. Cl.
| | |
|---|---|
| *A23L 1/236* | (2006.01) |
| *C12P 19/44* | (2006.01) |
| *A24B 15/10* | (2006.01) |
| *C12P 19/14* | (2006.01) |
| *C12P 19/56* | (2006.01) |
| *A23L 27/30* | (2016.01) |

(52) U.S. Cl.
CPC ............... *C12P 19/44* (2013.01); *A23L 27/33* (2016.08); *A23L 27/36* (2016.08); *A24B 15/10* (2013.01); *C12P 19/14* (2013.01); *C12P 19/56* (2013.01)

(58) Field of Classification Search
CPC ........... C12P 19/44; C12P 19/14; C12P 19/56; A23L 27/33; A23L 27/36; A24B 15/10
USPC .............. 426/48, 49, 52, 425, 429, 431, 548
See application file for complete search history.

(56) References Cited

U.S. PATENT DOCUMENTS

| | | |
|---|---|---|
| 3,723,410 A | 3/1973 | Persinos |
| 4,082,858 A | 4/1978 | Morita et al. |
| 4,171,430 A | 10/1979 | Matsushita et al. |
| 4,219,571 A | 8/1980 | Miyake |
| 4,361,697 A | 11/1982 | Dobberstein et al. |
| 4,454,290 A | 6/1984 | Dubois |
| 4,590,160 A | 5/1986 | Nishihashi et al. |
| 4,599,403 A | 7/1986 | Kumar |
| 4,612,942 A | 9/1986 | Dobberstein et al. |
| 4,657,638 A | 4/1987 | le Grand et al. |
| 4,892,938 A | 1/1990 | Giovanetto |
| 4,917,916 A | 4/1990 | Hirao et al. |
| 5,112,610 A | 5/1992 | Kienle |
| 5,576,042 A | 11/1996 | Fuisz |
| 5,779,805 A | 7/1998 | Morano |
| 5,962,678 A | 10/1999 | Payzant et al. |
| 5,972,120 A | 10/1999 | Kutowy et al. |
| 6,031,157 A | 2/2000 | Morita et al. |
| 6,080,561 A | 6/2000 | Morita et al. |
| 6,204,377 B1 | 3/2001 | Nishimoto et al. |
| 6,228,996 B1 | 5/2001 | Zhou et al. |
| 6,706,304 B1 | 3/2004 | Ishida et al. |
| 7,807,206 B2 | 10/2010 | Magomet et al. |
| 7,838,011 B2 | 11/2010 | Abelyan et al. |
| 7,862,845 B2 | 1/2011 | Magomet et al. |
| 8,257,948 B1 | 9/2012 | Markosyan |
| 2002/0132320 A1 | 9/2002 | Wang et al. |
| 2003/0161876 A1 | 8/2003 | Hansson et al. |
| 2003/0236399 A1 | 12/2003 | Zheng et al. |
| 2006/0083838 A1 | 4/2006 | Jackson et al. |
| 2006/0134292 A1 | 6/2006 | Abelyan et al. |
| 2006/0142555 A1 | 6/2006 | Jonnala et al. |
| 2007/0082102 A1 | 4/2007 | Magomet et al. |
| 2007/0082103 A1 | 4/2007 | Magomet et al. |
| 2007/0116800 A1 | 5/2007 | Prakash |
| 2007/0116819 A1 | 5/2007 | Prakash |
| 2007/0116820 A1 | 5/2007 | Prakash |
| 2007/0116821 A1 | 5/2007 | Prakash |
| 2007/0116822 A1 | 5/2007 | Prakash |
| 2007/0116823 A1 | 5/2007 | Prakash |

(Continued)

FOREIGN PATENT DOCUMENTS

| | | |
|---|---|---|
| BR | P10701736 | 7/2008 |
| CN | 1049666 | 3/1991 |

(Continued)

OTHER PUBLICATIONS a-Glucosyltransferase Treated Stevia, Japan's Specifications and Standards for Food Additives, VIII edition, 2009, p. 257.

(Continued)

*Primary Examiner* — Leslie A Wong

(74) *Attorney, Agent, or Firm* — Briggs and Morgan, P.A.; Audrey J. Babcock

(57) ABSTRACT

The invention provides a process of producing Rubusoside from steviol glycosides of *Stevia rebaudiana* plant. The process is useful for producing high purity Rubusoside with purity greater than 95% (dry basis). High purity rubusoside is useful as in combination with other caloric and non-caloric sweeteners as well as non-caloric sweetener in various food and beverage compositions. The high purity rubusoside is useful as non-caloric sweetener in edible and chewable compositions such as any beverages, confectionaries, bakeries, cookies, chewing gums, and alike.

13 Claims, 1 Drawing Sheet

(56) References Cited

U.S. PATENT DOCUMENTS

| | | |
|---|---|---|
| 2007/0116824 A1 | 5/2007 | Prakash |
| 2007/0116825 A1 | 5/2007 | Prakash |
| 2007/0116826 A1 | 5/2007 | Prakash |
| 2007/0116827 A1 | 5/2007 | Prakash |
| 2007/0116828 A1 | 5/2007 | Prakash |
| 2007/0116829 A1 | 5/2007 | Prakash |
| 2007/0116830 A1 | 5/2007 | Prakash |
| 2007/0116831 A1 | 5/2007 | Prakash |
| 2007/0116832 A1 | 5/2007 | Prakash |
| 2007/0116833 A1 | 5/2007 | Prakash |
| 2007/0116834 A1 | 5/2007 | Prakash |
| 2007/0116835 A1 | 5/2007 | Prakash |
| 2007/0116836 A1 | 5/2007 | Prakash |
| 2007/0116837 A1 | 5/2007 | Prakash |
| 2007/0116838 A1 | 5/2007 | Prakash |
| 2007/0116839 A1 | 5/2007 | Prakash |
| 2007/0116840 A1 | 5/2007 | Prakash |
| 2007/0116841 A1 | 5/2007 | Prakash |
| 2007/0128311 A1 | 6/2007 | Prakash |
| 2007/0134390 A1 | 6/2007 | Prakash |
| 2007/0134391 A1 | 6/2007 | Prakash |
| 2007/0224321 A1 | 9/2007 | Prakash |
| 2007/0292582 A1 | 12/2007 | Prakash et al. |
| 2008/0064063 A1 | 3/2008 | Brandle et al. |
| 2008/0102497 A1 | 5/2008 | Wong et al. |
| 2008/0107775 A1 | 5/2008 | Prakash |
| 2008/0107776 A1 | 5/2008 | Prakash |
| 2008/0107787 A1 | 5/2008 | Prakash |
| 2008/0108710 A1 | 5/2008 | Prakash |
| 2008/0111269 A1 | 5/2008 | Politi et al. |
| 2008/0226797 A1 | 9/2008 | Lee et al. |
| 2008/0292764 A1 | 11/2008 | Prakash et al. |
| 2008/0292765 A1 | 11/2008 | Prakash |
| 2008/0292775 A1 | 11/2008 | Prakash |
| 2008/0300402 A1 | 12/2008 | Yang et al. |
| 2009/0017185 A1 | 1/2009 | Catani |
| 2009/0053378 A1 | 2/2009 | Prakash |
| 2009/0074935 A1 | 3/2009 | Lee |
| 2009/0079935 A1 | 3/2009 | Harris et al. |
| 2009/0142817 A1 | 6/2009 | Norman et al. |
| 2009/0226590 A1 | 9/2009 | Fouache et al. |
| 2010/0055752 A1 | 3/2010 | Kumar |
| 2010/0056472 A1 | 3/2010 | Duan et al. |
| 2010/0099857 A1 | 4/2010 | Evans et al. |
| 2010/0011215 A1 | 5/2010 | Abelyan et al. |
| 2010/0057024 A1 | 5/2010 | Cavallini et al. |
| 2010/0120710 A1 | 5/2010 | Watanabe et al. |
| 2010/0013756 A1 | 6/2010 | Prakash et al. |
| 2010/0018986 A1 | 7/2010 | Abelyan et al. |
| 2010/0189861 A1 | 7/2010 | Abelyan et al. |
| 2010/0227034 A1 | 9/2010 | Purkayastha et al. |
| 2010/0255171 A1 | 10/2010 | Purkayastha et al. |
| 2010/0278993 A1 | 11/2010 | Prakash et al. |
| 2010/0316782 A1 | 12/2010 | Shi et al. |
| 2011/0030457 A1 | 2/2011 | Valery et al. |
| 2011/0033525 A1 | 2/2011 | Lui |
| 2011/0092684 A1 | 4/2011 | Abelyan et al. |
| 2011/0104353 A1 | 5/2011 | Lee |
| 2011/0111115 A1 | 5/2011 | Shi et al. |
| 2011/0124587 A1 | 5/2011 | Jackson et al. |
| 2011/0160311 A1 | 6/2011 | Prakash et al. |
| 2011/0189360 A1 | 8/2011 | Yoo et al. |
| 2011/0195169 A1 | 8/2011 | Markosyan et al. |
| 2012/0164678 A1 | 6/2012 | Stephanopoulos et al. |
| 2012/0214752 A1 | 8/2012 | Markosyan |

FOREIGN PATENT DOCUMENTS

| | | |
|---|---|---|
| CN | 1100727 | 3/1995 |
| CN | 1112565 | 11/1995 |
| CN | 1192447 | 9/1998 |
| CN | 1238341 | 12/1999 |
| CN | 1349997 | 5/2002 |
| CN | 101200480 | 6/2008 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 62166861 | 7/1987 |
| JP | 63173531 | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | 2008091547 | 7/2008 |
| WO | 2009108680 | 9/2009 |
| WO | 2010118218 | 10/2010 |
| WO | 2011059954 | 5/2011 |
| WO | 2011153378 | 12/2011 |
| WO | 2012082493 | 6/2012 |
| WO | 2012082677 | 6/2012 |
| WO | 2013022989 | 2/2013 |

OTHER PUBLICATIONS

Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.

Chang, S. S. et al., "Stability Studies of Stevioside and Rebaudioside A in Carbonated Beverages", Journal of Agricultural and Food Chemistry, vol. 31, 1983, 409-412.

Chen, et al., "Enrichment and separation of rebaudioside A from stevia glycosides by a novel adsorbent with pyridyl group", Science in China, vol. 42, No. 3 1999, 277-282.

Chen, et al., "Selectivity of polymer adsorbent in adsorptive separations of stevia diterpene glycisides", Science in China, vol. 41, No. 4 1998, 436-441.

(56) References Cited

OTHER PUBLICATIONS

Chen, et al., "Studies on the adsorptive selectivity of the polar resin with carbonyl group on rebaudioside A", Acta Polymeric Scnica, No. 4 1999, 398-403.
Crammer, et al., "Sweet glycosides from the *Stevia* plant", Chemistry in Britain, Oct. 1986, 915-916, 918.
Darise et al., "Enzymic Transglucosylation of Rubusoside and the Structure-Sweetness Relationship of Steviol Bisglycosides," Agric. Biol. Chem. vol. 48(10), 1984, 2483-2488.
Dubois et al., "Diterpenoid Sweeteners. Synthesis and Sensory Evaluation of Stevioside Analogues with Improved Organoleptic Properties," J. Med. Chem. vol. 28, (1985) 93-98.
Fuh, , "Purification of steviosides by membrane and ion exchange process", Journal of Food Science, vol. 55, No. 5 1990, 1454-1457.
Fukunaga et al., "Enzymic Transglucosylation Products of Stevioside: Separation and Sweetness-evaluation," Agric. Biol. Chem. vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of Bacillus Macerans", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063, dated Aug. 5, 2011.
International Search Report and Written Opinion of PCT/US2011/047498, dated Dec. 22, 2011.
International Search Report and Written Opinion of PCT/US2011/047499, dated Dec. 22, 2011.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
Jaitak, et al., "An Efficient Microwave-assisted Extraction Process of Stevioside and Rebaudioside-A from Stevia Rebaudiana (Bertoni)", Phytochem. Anal. vol. 20 2009, 240-245.
Kennelly, "Sweet and non-sweet constituents of Stevia rebaudiana", *Stevia*: The genus *Stevia*, Taylor & Francis, 2002, 68-85.
Kinghorn, "Overview", Stevia: The genus *Stevia*, Taylor & Francis, 2002, 1-17.
Kitahata, S. et al., "Production of Rubusoside Derivatives by Transgalactosylation of Various b-Galactosidases", Agric. Biol. Chem., vol. 53, No. 11 1989, 2923-2928.
Kobayashi, et al., "Dulcoside A and B, New diterpene glycosides from Stevia Rebaudiana", Phytochemistry, vol. 16 1977, 1405-1408.
Kochikyan, et al., "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.
Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chem., vol. 55, No. 12 1991, 2959-2965.
Montovaneli, et al., "The effect of temperature and flow rate on the clarification of the aqueous Stevia-extract in fixed-bed column with zeolites", Brazilian Journal of Chemical Engineering, vol. 21, No. 3 2004, 449-458.
Moraes, et al., "Clarification of Stevia rebaudiana (Bert.) Bertoni extract adsorption in modified zeolites", Acta Scientiarum, vol. 23, No. 6 2001, 1375-1380.
Ohta et al., "Characterization of Novel Steviol Glycosides from Leaves of Stevia rebaudiana Morita," J. Appl. Glycosi., vol. 57, 199-209, 2010.
Ohtani et al. "Chapter 7. Methods to improve the taste of the sweet principles of Stevia rebaudiana." The Genus *Stevia*, edited by A. Douglas Kinghorn, CRC Press 2001, Taylor and Francis, London and New York, pp. 138-159.
Phillips, K. C. , "Stevia: steps in developing a new sweetener", In T.H. Grenby, Editor, Developments in Sweeteners—3, Elsevier 1987, 1-43.
Pol, et al., "Comparison of two different solvents employed for pressurised fluid extraction of stevioside from Stevia rebaudiana: methanol versus water", Anal Bioanal Chem vol. 388 2007, 1847-1857.
Prakash et al., "Development of rebiana, a natural, non-caloric sweetener," Jul. 1, 2008, Food and Chemical Toxicology, vol. 46, Is. 7, Sup. 1, p. S75-S82.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of Stevia Rebaudiana", Chem. Pharm. Bull., vol. 25, 1977, 844-846.
Shi, et al., "Synthesis of bifunctional polymeric adsorbent and its application in purification of Stevia glycosides", Reactive & Functional Polymers, vol. 50 2002, 107-116.
Shibata et al., "Glucosylation of Steviol and Steviol-Glucosides in Extracts from Stevia rebaudiana Bertoni," Plant Physiol. vol. 95, (1991) 152-156.
Starratt, et al., "Rebaudioside F, a diterpene glycoside from Stevia Rebaudiana", Phytochemistry, vol. 59 2002, 367-370.
Sweet Green Fields, LLC, "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdata.fda.gov/scripts/fcn/gras_notices/grn000282.pdf (obtained from the Web on May 8, 2012) entire document esp. p. 22, Table 1.
Tanaka, O. , "Improvement of taste of natural sweeteners", Pure & Appl. Chem., vol. 69, No. 4 1997, 675-683.
Teo, et al., "Validation of green-solvent extraction combined with chromatographic chemical fingerprint to evaluate quality of Stevia rebaudiana Bertoni", J. Sep. Sci, vol. 32 2009, 613-622.
United Nations' Food and Agriculture Organization/Joint Expert Committee on Food Additives (2010) Steviol Glycosides, Compendium of Food Additive Specifications, FAO JECFA Monographs 10, 17-21.
van der Maarel et al., "Properties and applications of starch-converting enzymes of the a-amylase family," Journal of Biotechnology, vol. 94 (2002) 137-155.

(56) References Cited

OTHER PUBLICATIONS

Vasquez, Stimulation of the Gerbil's Gustatory Receptors by Some Potently Sweet Terpenoids, J. Agric. Food Chem., vol. 41, 1305-1310, 1993.

Yamamoto, K. et al., "Effective Production of Glycosyl-steviosides by a-1,6 Transglucosylation of Dextrin Dextranase", Biosci. Biotech. Biochem. vol. 58, No. 9 1994, 1657-1661.

Yoda, et al., "Supercritical fluid extraction from Stevia rebaudiana Bertoni using $CO_2$ and $CO_2$+ water: extraction kinetics and identification of extracted components", Journal of Food Engineering, vol. 57 2003, 125-134.

Zell, et al., "Investigation of Polymorphism in Aspartame and Neotame Using Solid-State NMR Spectroscopy", Tetrahedron, vol. 56, 2000, 6603-6616.

Zhang, et al., "Membrane-based separation scheme for processing sweetener from *Stevia* leaves", Food Research International, vol. 33 2000, 617-620.

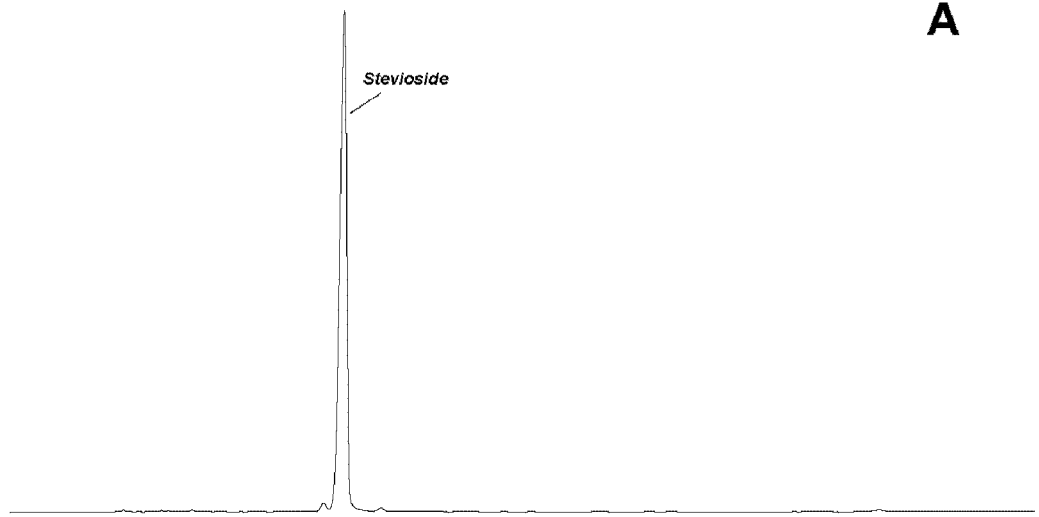
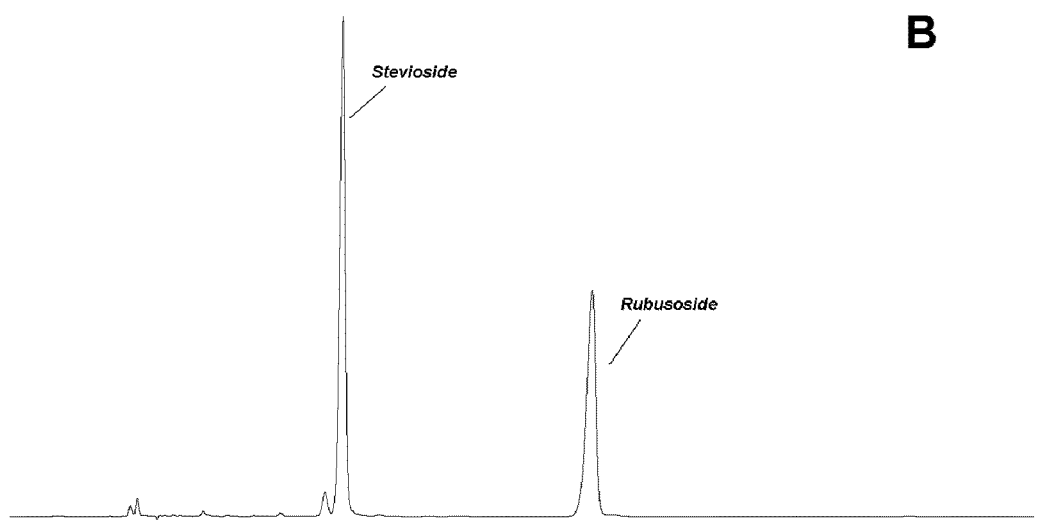
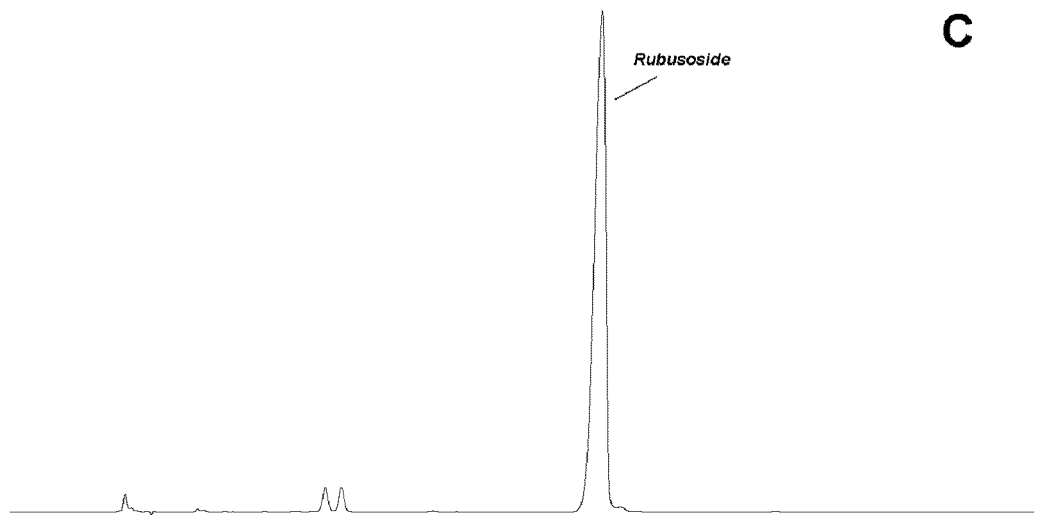

PROCESS FOR PRODUCING HIGH-PURITY RUBUSOSIDE

This application is continuation-in-part of, and claims the benefit of priority from, the following applications: U.S. patent application Ser. No. 14/380,071, filed on Aug. 21, 2014, which is a U.S. National Stage application filed under 35 U.S.C. § 371 based on PCT/MY2013/000051, filed on Mar. 7, 2013, claiming the benefit of priority of U.S. Provisional Patent Application No. 61/608,110, filed on Mar. 8, 2012; and U.S. patent application Ser. No. 13/553,820, filed on Jul. 20, 2012 now U.S. Pat. No. 8,993,028, claiming the benefit of priority of U.S. Provisional Patent Application No. 61/522,237, filed on Aug. 10, 2011.

FIELD OF THE INVENTION

The invention relates to a process for producing steviol glycosides, more particularly Rubusoside from steviol glycosides of *Stevia rebaudiana* plant.

BACKGROUND OF THE INVENTION

Nowadays high intensity sweeteners are used worldwide. They can be of both synthetic and natural origin.

Non-limiting examples of synthetic sweeteners include sucralose, potassium acesulfame, aspartame, alitame, saccharin, neohesperidin dihydrochalcone synthetic derivatives, cyclamate, neotame, dulcin, suosan, N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and the like.

Non-limiting examples of natural high intensity sweeteners include Stevioside, Rebaudioside A, Rebaudioside B, Rebaudioside C, Rebaudioside E, Rebaudioside F, Steviolbioside, Dulcoside A, Rubusoside, mogrosides, brazzein, neohesperidin dihydrochalcone (NHDC), glycyrrhizic acid and its salts, thaumatin, perillartine, pernandulcin, mukuroziosides, baiyunoside, phlomisoside-I, dimethyl-hexahydrofluorene-dicarboxylic acid, abrusosides, periandrin, carnosiflosides, cyclocarioside, pterocaryosides, polypodoside A, brazilin, hernandulcin, phillodulcin, glycyphyllin, phlorizin, trilobatin, dihydroflavonol, dihydroquercetin-3-acetate, neoastilibin, trans-cinnamaldehyde, monatin and its salts, selligueain A, hematoxylin, monellin, osladin, pterocaryoside A, pterocaryoside B, mabinlin, pentadin, miraculin, curculin, neoculin, chlorogenic acid, cynarin, siamenoside and others.

*Stevia rebaudiana* Bertoni is a perennial shrub of the Asteraceae (Compositae) family native to certain regions of South America. The leaves of the plant contain from 10 to 20% of diterpene glycosides, which are around 150 to 450 times sweeter than sugar. The leaves have been traditionally used for hundreds of years in Paraguay and Brazil to sweeten local teas and medicines.

The extract of *Stevia rebaudiana* plant contains a mixture of different sweet diterpene glycosides, which have a single base-steviol and differ by the presence of carbohydrate residues at positions C13 and C19. These glycosides accumulate in *Stevia* leaves and compose approximately 10%-20% of the total dry weight. Typically, on a dry weight basis, the four major glycosides found in the leaves of *Stevia* are Dulcoside A (0.3%), Rebaudioside C (0.6-1.0%), Rebaudioside A (3.8%) and Stevioside (9.1%). Other glycosides identified in *Stevia* extract include Rebaudioside B, D, E, and F, Steviolbioside and Rubusoside. Among steviol glycosides only Stevioside and Rebaudioside A are available in commercial scale.

The physical and sensory properties are well studied only for Stevioside and Rebaudioside A. The sweetness potency of Stevioside is around 210 times higher than sucrose, Rebaudioside A in between 200 and 400 times.

On the other hand commercial preparations of steviol glycosides such as *Stevia* Extract, Rebaudioside A possess certain drawbacks substantially limiting their usage in mainstream products.

It has to be noted that high intensity sweeteners' taste profile is highly dependant on the concentration and usually the higher the concentration the higher the sensation of undesirable taste components such as bitterness, licorice, lingering aftertaste. This phenomenon limits the usage of steviol glycosides further to 4-5% sucrose equivalents in order to achieve pleasant taste of a food or beverage sweetened with *stevia* sweeteners.

Therefore in many cases various sweeteners are used in blends to benefit from the effect of synergism, which allows the usage of sweeteners at lower concentrations where undesirable taste profile attributes are less prominent. It has to be noted that synergistic effect can be achieved both between different high intensity sweeteners as well as between high intensity and bulk sweeteners such as sucrose etc.

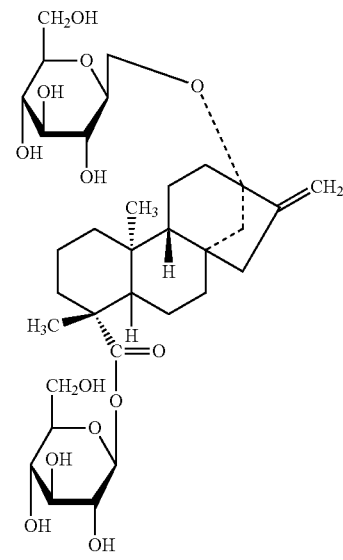

RUBUSOSIDE

Rubusoside (CAS No: 64849-39-4), is one of sweet sweet glycosides found in *Stevia rebaudiana*. Its concentration in dried leaves of *Stevia* is usually <0.2%. However rubusoside is also found in leaves of *Rubus suavissimus* S. Lee (Chinese sweet leaf). Rubusoside is the main steviol glycoside found in the leaves of *Rubus suavissimus*.

Recent studies show that Rubusoside possess certain valuable properties. Particularly WIPO Patent Application WO/2011/090709 describes sweetness-enhancing properties of Rubusoside. U.S. patent application Ser. No. 12/937,055 now abandoned, describe Rubusoside usage as a natural solubilizing agent for a number of compounds.

These properties multiply the significance of Rubusoside and attract great interest for processes of preparation of highly purified forms of Rubusoside.

There are few processes described in for Rubusoside preparation.

WIPO Patent Application WO/2011/090709 describes a process for preparing high purity rubusoside wherein the commercial crude Rubusoside extract (63.7% purity) was dissolved in aqueous methanol and subjected to chromatographic purification on a column packed with reverse-phase stationary phase. The fractions with high Rubusoside content were combined, dried and refluxed with methanol, to prepare Rubusoside having 94.6% purity. It has to be noted that employing chromatographic separation techniques in large scale production is not feasible and is suitable generally for Lab or pilot scale processes.

U.S. patent application Ser. No. 12/937,055 now abandoned, describes a process for Rubusoside preparation wherein *Rubus suavissimus* dried leaves were extracted with water and the water extract was dried to yield a crude extract containing 5-15% rubusoside (w/w). The dried crude extract was dissolved in water and subjected to column chromatography with macroporus adsorbent. As a result Rubusoside was adsorbed on macroporous resin and subsequently eluted with ethanol to obtain a purified extract containing ca. 60% rubusoside. Subsequently, the purified extract was subjected to chromatography on a column packed with silicagel and the fractions rich in Rubusoside were dried to yield Rubusoside with ca. 80% purity. The said material was further re-crystallized from Methanol to yield rubusoside with >99% purity. As discussed above, processes utilizing chromatographic techniques are suitable for Lab or pilot scale production only.

In all above-mentioned inventions Rubusoside is derived from *Rubus suavissimus* leaf extracts. It has to be noted that the supply and availability of *Rubus suavissimus* leaves is somewhat limited.

On the other hand the extracts and purified glycosides of *Stevia rebaudiana* are relatively easy to obtain. Particularly there's a large and cheap supply of high purity Stevioside (98%) and *Stevia rebaudiana* extracts containing high levels of Stevioside (up to 80%). The cultivation of *Stevia rebaudiana* is much simpler and currently there are Stevia commercial growers in various regions of the world.

Thus it can be concluded, there is a need for a simple, efficient, and economical process for production of high purity Rubusoside from easily accessible raw materials.

SUMMARY OF THE INVENTION

The invention relates to a process for production of steviol glycosides, and more particularly to a process for production of Rubusoside.

The primary objective of the invention is to develop an efficient process of producing Rubusoside from glycosides of *Stevia rebaudiana*.

One aspect of present invention provides a process of biocatalytic conversion of Stevioside to Rubusoside. In one embodiment the process comprises the steps of:

I. providing initial steviol glycosides such as highly purified Stevioside or an extract of *Stevia rebaudiana* containing Stevioside, or a mixture of steviol glycosides one of which is Stevioside;

II. dissolving the initial steviol glycosides in the water;

III. providing an enzyme with glycosyl hydrolase activity to obtain reaction mixture;

IV. incubating the reaction mixture to facilitate complete or partial transformation of Stevioside to Rubusoside;

V. terminating the reaction by thermal inactivation of enzyme;

VI. recovering and purifying highly purified Rubusoside from reaction mixture.

Another aspect of the present invention provides a process for recovery and purification of Rubusoside from reaction mixture. In one embodiment the process comprises the steps of:

i. providing reaction mixture containing Rubusoside;

ii. contacting the reaction mixture with macroporous adsorbent resin;

iii. eluting the adsorbed Rubusoside with aqueous alcohol;

iv. removing the alcohol from eluate and drying the solution to yield a purified Rubusoside.

In yet another embodiment, the recovery and purification process comprises steps of:

a. providing reaction mixture containing Rubusoside;

b. drying the reaction mixture;

c. dissolving the extract in a first aqueous alcoholic solution to obtain a first mixture;

d. inducing crystallization in the first mixture by temperature gradient treatment;

e. filtering the first mixture to obtain a first precipitate and a first filtrate;

f. dissolving the first precipitate in a second aqueous alcoholic solution to obtain a second mixture;

g. adding activated carbon to second mixture and filtering it to obtain decolorized second mixture;

h. inducing crystallization in the decolorized second mixture by temperature gradient treatment;

i. filtering the decolorized second mixture to obtain a second precipitate and a second filtrate;

j. suspending the second precipitate in a third aqueous alcoholic solution to obtain a third mixture;

k. filtering the third mixture to obtain a third precipitate and a third filtrate; and l. drying the third precipitate to yield purified Rubusoside.

In another embodiment of the process, the first aqueous alcoholic solution in step (c) is an methanol-water solution, with 75-99% methanol.

In another embodiment of the process, the second aqueous alcoholic solution in step (f) is a methanol-water solution with 70-90% methanol.

In another embodiment of the process, the third aqueous alcoholic solution in step (j) is a methanol-water solution with 90-99% methanol.

In another embodiment of the process, in steps (d) and (h) inducing crystallization comprises increasing the mixture temperature to 65-70° C. then gradually cooling it to about 0-40° C. at a rate of about 1-20° C. per hour with continuous mild agitation.

In another embodiment of the process, the aqueous alcoholic solution comprises one or more organic solvents selected from the group consisting of methanol, ethanol, 1-propanol, and isopropanol.

In another embodiment of the process, the purified Rubusoside has purity greater than 95% on a dry basis.

In another embodiment of the process, the purified Rubusoside has purity greater than 98% on a dry basis.

Another aspect of the present invention provides a product comprising high purity Rubusoside, wherein the product is selected from the group consisting of food, beverage, pharmaceutical composition, tobacco, nutraceutical, oral hygienic composition, or cosmetic.

Another aspect of the present invention provides a sweetener composition comprising high purity Rubusoside.

In another embodiment, the sweetener composition further comprises Rebaudioside A, enzymatically modified stevia, Rebaudioside D, a mixture of steviol glycosides with more than 95% (on dry basis) total steviol glycosides content, high intensity sweetener and natural flavor compound, caloric sweetener, or sucrose.

In another embodiment, the sweetener composition further comprises one natural high intensity sweetener selected from the group consisting of: steviol glycosides including a purified sweet steviol glycoside mixture, stevioside, rebaudioside A, rebaudioside B, rebaudioside C, rebaudioside D, rebaudioside E, rebaudioside F, dulcoside A, dulcoside B, stevia, alpha-glucosyl stevia, fructosyl stevia, galactosyl stevia, beta-glucosyl stevia; siamenoside; mogroside IV; mogroside V; Luo Han Guo sweetener; monatin and its salts (monatin SS, RR, RS, SR); glycyrrhizic acid and its salts; curculin; thaumatin; monellin; mabinlin; brazzein; hernandulcin; phyllodulcin; glycyphyllin; phloridzin; trilobatin; baiyunoside; osladin; polypodoside A; pterocaryoside A; pterocaryoside B; mukurozioside; phlomisoside I; periandrin I; abrusoside A; cyclocarioside I; and combinations thereof.

It is to be understood that the described biocatalytic conversion process can be applied also to other steviol glycosides wherein the hydrolytic action of various glycosyl hydrolases can produce new steviol glycosides' molecules.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 1 shows HPLC chromatograms of reaction mixture after 0 hrs (A), 6 hrs (B) and 24 hrs (C).

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention provides a process for production and purification of rubusoside.

In one embodiment of present invention, the process of the isolation and purification begins with providing Stevioside derived from Stevia rebaudiana extract, containing 90-100%, preferably 95-99% (on dry basis) Stevioside.

Stevioside is dissolved in water to obtain a solution with 1-50%, preferably 5-30%, more preferably 8-10% (wt/vol) concentration. The pH of the solution is adjusted to pH 3.0-8.0 preferably pH 4.5-6.5 and the temperature is maintained at 28-50° C., preferably 35-45° C. An enzyme with glycosyl hydrolase activity is added to solution to make reaction mixture. Non-limiting examples of enzymes include, rhamnosidase, β-glucosidase, hesperidinase, naringinase, pectinase, cellulase, and others, in free or immobilized forms. The reaction mixture is maintained at pH 3.0-8.0 preferably pH 4.5-6.5 and the temperature is maintained at 28-50° C., preferably 35-45° C., for about 12-24 hours, or long enough to allow the desired degree of conversion of Stevioside to Rubusoside occur. Upon completion the reaction mixture is boiled at 100° C. for 10-30 min to inactivate the enzyme and then filtered with activated carbon and spray dried. Alternatively the mixture can be additionally treated with ion exchange resins, purified by macroporous adsorption resins, membranes etc. The spray dried reaction mixture can be used "as-is" or subjected to further purification to prepare high purity Rubusoside.

For further purification the spray dried reaction mixture is admixed with a first aqueous alcoholic solution containing 70-100%, more preferably 75-99% alcohol to obtain a first mixture. The ratio (wt/vol) of spray dried reaction mixture to aqueous alcohol is 1:1 to 1:5, more preferably 1:2 to 1:4. The alcohol is selected from the group comprising ethanol, methanol, 1-propanol, 2-propanol or combinations thereof, more preferably ethanol and methanol.

In another embodiment the first mixture is incubated at a temperature 10-100° C. more preferably 30-80° C. for 0.5-30 min more preferably for 1-10 min.

In another embodiment the first mixture is then cooled to 0-40° C., preferably 10-20° C., at a rate of 1-20° C. per hour, preferably about 8-11° C. per hour, and incubated at final temperature for 1-72 hours, preferably 1-24 hours to facilitate the crystallization of Rubusoside.

In another embodiment the crystallized Rubusoside is separated from first mixture to become a first precipitate, and the remaining solution becomes a first filtrate.

In another embodiment the first precipitate has 75-99%, preferably 90-95% (on dry basis) Rubusoside content.

In another embodiment the first precipitate is admixed with a second aqueous alcoholic solution containing 60-100%, more preferably 70-90% alcohol to obtain a second mixture. The ratio (wt/vol) of first precipitate to aqueous alcohol is 1:1 to 1:5, more preferably 1:2 to 1:4. The alcohol is selected from the group comprising ethanol, methanol, 1-propanol, 2-propanol or combinations thereof, more preferably ethanol and methanol.

In another embodiment the second mixture is heated till full dissolution of first precipitate and 1-5%, preferably 1-2% of activated carbon is added and the mixture is incubated for 20 min at 60-70° C. Subsequently the activated carbon is removed by means of press filter to obtain decolorized second mixture.

In another embodiment the decolorized second mixture is incubated at a temperature 10-100° C. more preferably 30-80° C. for 0.5-30 min more preferably for 1-10 min.

In another embodiment the decolorized second mixture is then cooled to 0-40° C. preferably 10-20° C. at a rate of 1-20° C. per hour, preferably 8-11° C. per hour, and incubated at final temperature for 1-72 hours, preferably 1-24 hours to facilitate the crystallization of Rubusoside.

In another embodiment the crystallized Rubusoside is separated from decolorized second mixture to become a second precipitate, and the remaining solution becomes a second filtrate.

In another embodiment the second precipitate has 90-100%, preferably 95-100% (on dry basis) Rubusoside content.

In another embodiment the second precipitate is further suspended in a third aqueous alcoholic solution containing 70-100%, more preferably 90-99% alcohol to obtain a third mixture. The ratio (vol/vol) of second filtrate to aqueous alcohol is 1:0 to 1:5, more preferably 1:0 to 1:2. The alcohol is selected from the group comprising ethanol, methanol, 1-propanol, 2-propanol or combinations thereof, more preferably ethanol and methanol.

In another embodiment the third mixture is then incubated at 0-40° C. preferably 10-30° C. for 1-144 hours, preferably 24-72 hours.

In another embodiment the third mixture is separated into a third precipitate and a third filtrate, where the third precipitate has >98% rubusoside content (on dry basis).

In another embodiment the third precipitate is dried by any means known to art to provide dry crystalline powder.

The HPLC analysis of steviol glycosides was carried out as described in FAO JECFA Monographs 10 (2010), using an Agilent Technologies (USA) "1200 series" chromatograph, equipped with Luna C18(2) 100A (Phenomenex, USA) column (4.6×250 mm, 5 µm), using 32:68 (v/v) mixture of acetonitrile and 10 mmol/L sodium phosphate buffer (pH 2.6) as mobile phase, and UV detector at 210 nm.

The obtained rubusoside preparations can be used as sweetness enhancer, flavor enhancer and sweetener in various food and beverage products. Non-limiting examples of food and beverage products include carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fishmeat products, bottled and canned foods, tabletop sweeteners, fruits and vegetables.

Additionally the highly purified rubusoside preparations can be used in drug or pharmaceutical preparations and cosmetics, including but not limited to toothpaste, mouthwash, cough syrup, chewable tablets, lozenges, vitamin preparations, and the like.

The highly purified rubusoside preparations can be used "as-is" or in combination with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, dulcoside A, steviolbioside, as well as other steviol glycosides found in *Stevia rebaudiana* Bertoni plant and mixtures thereof, *stevia* extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, lactose, aspartame, saccharin, sucralose, sugar alcohols.

Non-limiting examples of flavors include lemon, orange, fruity, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents.

The following examples illustrate preferred embodiments of the invention.

Example 1

Biocatalytic Preparation of Rubusoside from Stevioside 20 g of Stevioside extract produced by "PureCircle Sdn Bhd" (Malaysia), containing 98.1% (on dry basis) Stevioside, and 1.2% Rebaudioside A was dissolved in 200 ml, of water and mixture was heated to 80° C. and maintained for 10 min until complete dissolution. Then the mixture was cooled to 37° C. and the pH was adjusted to pH 5.0. 20 Units (about 6 g) of "Hesperidinase from *Aspergillus niger*" (Sigma-Aldrich PN H8137) was added and the reaction mixture was incubated at 37° C. under continuous agitation. After 24 hrs the HPLC analysis of reaction mixture sample, showed 98% of Stevioside conversion to Rubusoside. The reaction mixture was boiled at 100° C. for 15 min and then cooled down to 80° C. 2 g of activated carbon was added and the reaction mixture was incubated for 30 min at 80° C. and then the carbon was separated by filtration. The obtained filtrate was evaporated under vacuum to about 30% total solids and spray dried to produce about 24 g powder containing about 59.9% rubusoside (dry basis).

Example 2

Purification of Rubusoside 10 g of spray dried reaction mixture prepared as per EXAMPLE 1 and containing 59.9% Rubusoside was dissolved in 200 mL of water and the solution was passed through a column packed with 200 mL Amberlite XAD 7HP macroporous adsorbent. The column was washed with 3 BV of water and the adsorbed Rubusoside was eluted with 300 mL 70% Ethanol. The Ethanol was evaporated and the obtained aqueous solution was dried to yield about 6 g of dry matter with 96.3% rubusoside content (dry basis).

Example 3

Purification of Rubusoside 10 g of spray dried reaction mixture prepared as per EXAMPLE 1 and containing 59.9% Rubusoside, was dissolved in 30 mL of 98% methanol and the mixture was heated to 60° C. and maintained for 10 min. Then the mixture was cooled to 10° C. at a rate of 10° C. per hour. During the cooling the mixture was subjected to continuous moderate agitation. Starting from about 15° C. fine crystals were formed. The amount of crystals subsequently increased. The mixture was incubated at 10° C. during 24 hrs. The crystals were separated by filtration and washed on the filter by pure methanol preliminarily chilled to 4° C. The obtained crystals were dried under vacuum at 80° C. to yield about 6.1 g crystals with 94.5% rubusoside content (dry basis).

Example 4

Refining of Rubusoside 5 g of Rubusoside prepared as per EXAMPLE 3 was suspended in 1000 mL of 92% methanol at room temperature. The mixture was heated and maintained at 30° C. during 48 hours. The crystals were separated by filtration and washed on the filter by pure methanol. The obtained crystals were dried under vacuum at 80° C. to yield about 4.1 g crystals with 98.5% rubusoside content (dry basis).

Example 5

Biocatalytic Preparation of Rubusoside from Stevioside 20 g of Stevioside extract produced by "PureCircle Sdn Bhd" (Malaysia), containing 98.1% (on dry basis) Stevioside, and 1.2% Rebaudioside A was dissolved in 200 ml, of water and mixture was heated to 80° C. and maintained for 10 min until complete dissolution. Then the mixture was cooled to 50° C. and the pH was adjusted to pH 5.5. 2,000 β-glucanase units (FBG; about 20 g) of "Viscozyme® L" (an enzyme preparation comprising β-glucanase, cellulase, hemicellulase, xylanase, produced by Novozymes, Denmark) was added and the reaction mixture was incubated at 50° C. under continuous agitation. After 48 hrs the HPLC analysis of reaction mixture sample, showed 99% of Stevioside conversion to Rubusoside.

I claim:

1. A process for preparing Rubusoside from steviol glycosides of *Stevia rebaudiana* comprising the steps of:
   A) providing a solution comprising Stevioside;
   B) adding 2000 fungal β-glucanase (FBG) units of an enzyme composition having fungal β-glucanase activity to the solution comprising Stevioside to obtain a reaction mixture; and
   C) incubating the reaction mixture at 28-50° C. for 12-48 hours to facilitate transformation of Stevioside to Rubusoside to obtain a reaction mixture containing Rubusoside.

2. The process of claim 1 wherein in step A) the concentration of Stevioside is 1-50% (wt/vol).

3. The process of claim 1 wherein in step C) the molar yield of Rubusoside from Stevioside is 1-100%.

4. The process of claim 1 further comprising:
   D) at least one purification technique employed on the reaction mixture containing Rubusoside, selected from the group comprising ion exchange treatment, macroporous adsorbent treatment, membrane process, chromatographic separation, and crystallization from various solvent systems to obtain a purified Rubusoside.

5. The process of claim 1 further comprising:
   D) recovery and purification of Rubusoside comprising the steps of:
      a) providing the reaction mixture containing Rubusoside;
      b) contacting the reaction mixture containing Rubusoside with macroporous adsorbent resin;
      c) eluting the adsorbed Rubusoside with aqueous alcohol to obtain an eluate;
      d) removing the alcohol from the eluate and drying the eluate to yield the purified Rubusoside.

6. The process of claim 1 further comprising:
   D) recovery and purification of Rubusoside comprising the steps of:
      a) providing a dried reaction mixture containing Rubusoside;
      b) dissolving the dried reaction mixture in a first aqueous alcoholic solution to obtain a first mixture;
      c) inducing crystallization in the first mixture by temperature gradient treatment;
      d) filtering the first mixture to obtain a first precipitate and a first filtrate;
      e) dissolving the first precipitate in a second aqueous alcoholic solution to obtain a second mixture;
      f) adding activated carbon to the second mixture and filtering it to obtain a decolorized second mixture;
      g) inducing crystallization in the decolorized second mixture by temperature gradient treatment;
      h) filtering the decolorized second mixture to obtain a second precipitate and a second filtrate;
      i) suspending the second precipitate in a third aqueous alcoholic solution to obtain a third mixture;
      j) filtering the third mixture to obtain a third precipitate and a third filtrate; and
      k) a drying the third precipitate to yield the purified Rubusoside.

7. The process of claim 6 wherein the first aqueous alcoholic solution in step b) is a methanol-water solution, with 75-99% methanol.

8. The process of claim 6 wherein the second aqueous alcoholic solution in step e) is a methanol-water solution with 70-90% methanol.

9. The process of claim 6 wherein the third aqueous alcoholic solution in step i) is a methanol-water solution with 90-99% methanol.

10. The process of claim 6 wherein steps c) and g) inducing crystallization comprises increasing the mixture temperature to 65-70° C. then gradually cooling it to 0-40° C., at a rate of 1-20° C. per hour with continuous mild agitation.

11. The process of claim 6 wherein the aqueous alcoholic solution comprises one or more organic solvents selected from the group consisting of methanol, ethanol, 1-propanol, and isopropanol.

12. The process of claim 1, wherein the purified Rubusoside has a purity greater than 95% on a dry basis.

13. The process of claim 1, wherein the purified Rubusoside has a purity greater than 98% on a dry basis.

* * * * *